(12) United States Patent
Atkinson et al.

(10) Patent No.: US 8,921,778 B2
(45) Date of Patent: Dec. 30, 2014

(54) DETECTION APPARATUS

(71) Applicant: Smiths Detection-Watford Limited, London (GB)

(72) Inventors: Jonathan Richard Atkinson, Watford (GB); Alastair Clark, Watford (GB); Stephen John Taylor, Hyde Heath (GB); William Angus Munro, Watford (GB)

(73) Assignee: Smiths Detection-Watford Limited, London (GB)

( * ) Notice: Subject to any disclaimer, the term of this patent is extended or adjusted under 35 U.S.C. 154(b) by 0 days.

(21) Appl. No.: 13/858,288

(22) Filed: Apr. 8, 2013

(65) Prior Publication Data

US 2014/0008527 A1   Jan. 9, 2014

Related U.S. Application Data

(63) Continuation of application No. 13/094,592, filed on Apr. 26, 2011, now Pat. No. 8,436,299, which is a continuation of application No. 11/918,940, filed as application No. PCT/GB2006/001442 on Apr. 20, 2006, now Pat. No. 7,932,489.

(30) Foreign Application Priority Data

Apr. 23, 2005   (GB) .................................. 0508239.1

(51) Int. Cl.
*H01J 49/40* (2006.01)
*G01N 27/62* (2006.01)
*G01N 27/68* (2006.01)

(52) U.S. Cl.
CPC .............. *G01N 27/622* (2013.01); *G01N 27/68* (2013.01); *H01J 49/40* (2013.01); *G01N 27/62* (2013.01)

USPC ............ 250/290; 250/281; 250/282; 250/287

(58) Field of Classification Search
CPC .. G01N 27/622; H01J 49/004; H01J 49/0045; H01J 49/005; H01J 49/0054; H01J 49/0059; H01J 49/0063; H01J 49/0068; H01J 49/0072; H01J 49/0077
USPC ......................................................... 250/287
See application file for complete search history.

(56) References Cited

U.S. PATENT DOCUMENTS 4,551,624 A   11/1985  Spangler et al.
5,245,192 A    9/1993  Houseman
(Continued)

FOREIGN PATENT DOCUMENTS

WO   WO-00/79261 A1    12/2000
WO   WO-2004/097396 A1  11/2004

OTHER PUBLICATIONS

Non-Final Office Action U.S. Appl. No. 13/094,592 dated Jun. 14, 2012.
(Continued)

*Primary Examiner* — Jack Berman
(74) *Attorney, Agent, or Firm* — Foley & Lardner LLP

(57) ABSTRACT

An ion mobility spectrometer has a pair of electrodes and midway along the drill chamber. A high field is applied between the electrodes and sufficient to modify ions in the region of the electrodes such that they move at a different rate towards the collector plate. This is used to modify the time of flight of selected ions or ion clusters and enable identification of ambiguous peaks on the IMS spectrum.

20 Claims, 1 Drawing Sheet

(56) References Cited

U.S. PATENT DOCUMENTS

| | | | |
|---|---|---|---|
| 5,304,797 A * | 4/1994 | Irie et al. | 250/287 |
| 5,338,931 A | 8/1994 | Spangler et al. | |
| 6,323,482 B1 | 11/2001 | Clemmer et al. | |
| 6,690,004 B2 | 2/2004 | Miller et al. | |
| 6,717,130 B2 * | 4/2004 | Bateman et al. | 250/282 |
| 6,949,743 B1 | 9/2005 | Schwartz | |
| 7,019,286 B2 | 3/2006 | Fuhrer et al. | |
| 7,129,482 B2 | 10/2006 | Miller et al. | |
| 7,932,489 B2 | 4/2011 | Atkinson et al. | |
| 7,946,150 B2 * | 5/2011 | Atkinson et al. | 73/19.01 |
| 8,436,299 B2 * | 5/2013 | Atkinson et al. | 250/287 |
| 8,455,816 B2 * | 6/2013 | Taylor et al. | 250/286 |
| 8,716,656 B2 * | 5/2014 | Peng et al. | 250/288 |
| 2002/0014586 A1 | 2/2002 | Clemmer | |
| 2003/0209665 A1 | 11/2003 | Losch et al. | |
| 2004/0032211 A1 | 2/2004 | Langford et al. | |

OTHER PUBLICATIONS

Notice of Allowance U.S. Appl. No. 13/094,592 dated Jan. 7, 2013.

* cited by examiner

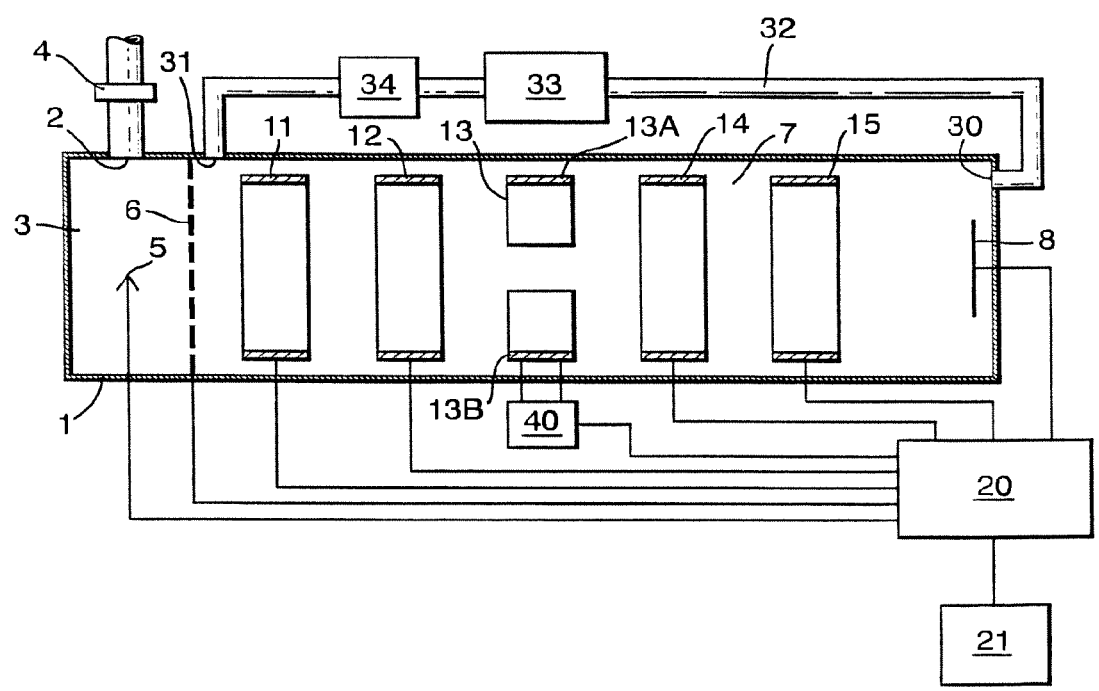

DETECTION APPARATUS

CROSS REFERENCE TO RELATED APPLICATIONS

The present application is a continuation application of U.S. application Ser. No. 13/094,592, filed on Apr. 26, 2011, which is the continuation of Ser. No. 11/918,940, filed on Oct. 22, 2007, now U.S. Pat. No. 7,932,489, which is the U.S. national stage of International Application No. PCT/GB2006/001442, filed on Apr. 20, 2006, which claims priority from United Kingdom Application No. 0508239.1 filed on Apr. 23, 2005. The entire disclosures of each of the-above-referenced applications are incorporated herein by reference.

This invention relates to detection apparatus of the kind for detecting substances in a sample.

The invention is more particularly, but not exclusively concerned with ion mobility spectrometers (IMSs).

Ion mobility spectrometers (IMSs) are used to detect the presence of small quantities of airborne chemicals in vapours or gases at atmospheric pressure. An IMS has some means to ionize the sample chemicals, such as a corona discharge or a radioactive source. A gate is opened to admit the molecular ion clusters into one end of a drift chamber across which a voltage is applied to cause the ion clusters to drift to the opposite end where they are collected on a collector plate. The molecular ion clusters might also include attached dopant ions. The time taken for a molecular ion cluster to pass from the gate to the collector plate is dependent on the mass, size, shape and charge on the molecular ion cluster. By measuring this time an indication can be provided of the nature of the chemical.

In many cases it can be difficult to identify positively the substance of interest because the time of flight of the ion clusters produced may be very similar to that of ion clusters of different substances. Various arrangements have been proposed for improving the discrimination between different molecular ion clusters. One arrangement described in U.S. Pat. No. 6,797,943 involves fragmenting the ions using laser energy, a pyrolyzer or the like. The ion clusters are accumulated in a reservoir where they are exposed to the ion modification energy prior to admittance to the drift chamber. One problem with this arrangement is that all the molecular ion clusters are subjected to fragmentation, which can lead to a large number of peaks on the spectrum, making analysis very difficult. Another problem with this arrangement is that a relatively large amount of energy is needed to ensure that fragmentation takes place, which can be a particular problem in portable, battery-powered apparatus.

It is an object of the present invention to provide alternative detection apparatus.

According to one aspect of the present invention there is provided detection apparatus of the above-specified kind, characterised in that the apparatus includes an electrical arrangement for subjecting molecules of the substances to an electrical field high enough to cause ion modification of some at least of the molecules.

The apparatus preferably includes an ionizer for ionizing the sample and an arrangement for measuring the mobility of the ions produced, the electrical arrangement causing ion modification of some at least of the ionized molecules. The electric field is preferably symmetrical and could be an RF field. The electric field could be applied in short bursts. The molecules may be individual molecules or clusters of molecules and may include attached dopant molecules. The electrical field may be arranged to cause modification of only selected ones of the molecules.

According to another aspect of the present invention there is provided detection apparatus for detecting substances in a sample, characterised in that the apparatus includes an arrangement for applying energy to molecules of the substance sufficient to cause ion modification of only selected ones of the molecules.

According to a further aspect of the present invention there is provided detection apparatus for detecting substances in a sample, characterised in that the apparatus is arranged to separate out molecules of different substances from one another into different regions of the apparatus and that the apparatus includes an arrangement for applying energy to a selected one of the regions sufficient to cause ion modification of only those molecules in that region.

According to a fourth aspect of the present invention there is provided ion mobility spectrometer apparatus including an ionization region, a gate, a drift chamber and a collector, characterised in that the apparatus includes a pair of electrodes spaced from one another across the apparatus, and that the apparatus is arranged to apply a high field between the electrodes sufficient to modify ions such that the modified ions travel at a different speed to the collector from unmodified ions.

The pair of electrodes may be located in the drift chamber. The apparatus may be arranged to apply the high field between the electrodes a predetermined time after opening the gate so that only ions with a selected range of mobilities are modified by the high field.

According to a fifth aspect of the present invention there is provided a method of detecting substances in a sample including the steps of applying energy to modify only selected molecules of the substances prior to detection.

The energy may be applied at times selected preferentially to cause ion modification of ions having selected ranges of mobility. The energy is preferably applied for short periods of time and/or at high frequency. The energy is preferably applied by means of an electrical field.

A time-of-flight ion mobility spectrometer according to the present invention will now be described, by way of example, with reference to the accompanying drawing, which shows the spectrometer schematically.

BRIEF DESCRIPTION OF THE DRAWINGS

FIG. 1 Illustrates an embodiment of an ion mobility spectrometer.

DESCRIPTION

The spectrometer includes an elongate, tubular housing 1 the interior of which is substantially at atmospheric pressure. An inlet port 2 towards its left-hand end opens into an ionisation region 3. A sample gas or vapour to be analysed is supplied to the port 2 via a filter 4, in the conventional manner. The ionisation region 3 includes a corona discharge point 5 or some other means, such as a radioactive source, for ionising the sample. A gate 6 separates the ionisation region 3 from a drift chamber 7, which extends to the right-hand end of the housing 1 where an ion collector plate 8 is mounted. The drift chamber 7 includes a row of electrodes 11 to 15 spaced from one another along the length of the drift chamber 7 in the usual way. The collector plate 8, electrodes 11 to 15, gate 6 and discharge point 5 are electrically connected to a processor control unit 20, which provides an output to a display or other utilisation unit 21 representative of the substances detected.

Drift gas is supplied to the right-hand end of the housing 1 at an inlet 30 to flow from right to left along the drift chamber 7, that is, in the opposite direction from the flow of ions. Drift gas is exhausted from the drift chamber 7 at its left-hand end through an outlet port 31.

Gas flows between the outlet port 31 and the inlet 30 via a gas system 32, which includes a molecular sieve 33 and a pump 34. The sieve 33 may contain a dopant in the manner described in W000/79261. Ions produced in the ionisation region 3 are admitted into the left-hand end of the drift chamber 7 when the gate 6 is opened. The ions drift from left to right along the drift chamber under the influence of the relatively low electrical field of about 250 V cm−1 applied by the electrodes 11 to 15. The ions of different mobilities separate out from one another as they pass along the drift chamber 7 so that, at anyone time, different ions will be in different regions of the chamber. The ions of different mobilities, therefore, reach the collector plate 8 at different times and produce output peaks to the processing unit 20 at different times.

As so far described, the apparatus is conventional.

The apparatus differs from previous apparatus by the inclusion of means to apply a high electrical field to cause ion modification of the ions, such as fragmentation. There are various ways in which this could be achieved. The high field could be applied at any part of the apparatus, but, in the present example, it is applied in the drift chamber 7. The field is applied by means of the electrode 13, which is separated into two electrodes 13A and 13B spaced from one another across the diameter of the drift chamber 7. Although these electrodes 13A and 13B are shown midway along the drift chamber 7, they could be located at any point along the chamber. These electrodes 13A and 13B are connected to a high voltage RF unit 40 controlled by the processing unit 20. The high voltage unit 40 is operable to apply a high strength RF field (typically around 2 MHz) effective to cause ion modification of a significant percentage of the ions within the field. The strength of the field is preferably at least 10,000 V/cm and may be of the order of several tens of thousands of volts per centimeter. The RF field may be applied continuously or in bursts of the order of 1 μs in order to prevent corona discharge. The symmetrical nature of the applied field is advantageous because it ensures that the molecular ion clusters remain substantially central within the drift chamber 7 and are not displaced to contact with the electrodes 13 to 15. Alternatively, non-RF intense short pulses of the order of 1 ns could be used. These fields enable sufficient energy to be transferred to the ions to cause ion modification. The modified or fragmented ions pass to the collector plate 8 with a different mobility from the unmodified ions and hence produce different peaks on the output spectrum. This can enable the apparatus to distinguish between two different ions having similar mobilities, since the modified versions of these ions will not generally have similar mobilities.

The sample gas or vapour could include a dopant selected to stabilise the neutral molecule environment in the device, such as water at a few hundred ppm.

The apparatus could be arranged to operate conventionally most of the time with the two electrodes 13A and 13B being at the same dc voltage, between the voltages on adjacent electrodes 12 and 14, that is, without the ion modification field. When an ambiguous substance is identified, the processing unit 20 would initiate the ion modification field in order to resolve the ambiguity. Alternatively, the apparatus could be operated with the ion modification field continuously on and then turn it off for short periods to confirm detection of a substance.

Application of the ion modification field could be coupled to operation of the gate 6. In such an arrangement, the ion modification field is initiated at a calculated predetermined time after opening the gate 6 such that only those ions within a selected range of mobilities are in the region of the ion modification field electrodes 13A and 13B when they are energized with the ion modification voltage. This arrangement helps confine the ion modification process to selected ions only, thereby avoiding too many peaks being produced on the spectrum and facilitating identification.

Alternative energy sources could be used to produce ion modification on selected ionized molecules in a similar manner. Such alternative energy sources could include: radiation sources, such as laser radiation, UV radiation, VUV radiation, infra-red or photo ionisation, electron bombardment, electron beams, electro spray, electron-ionisation, corona discharge, glow discharge, plasma or radioactive emission.

The ion modification field could be applied at any location, such as in the ionization region 3 or at the gate 6 and could be applied at any time during each scan of the IMS apparatus. The invention could be applied to detection apparatus other than IMS apparatus.

We claim:

1. A detection apparatus for detecting a substance in a sample, the detection apparatus comprising:
    an ionizer configured to ionize molecules of the substance; and
    an electrical arrangement configured to perform ion modification on ions produced by the ionizer so as to cause ion modification of at least some of the ions;
    wherein the detection apparatus is configured such that the electrical arrangement performs the ion modification only if the detection apparatus determines that there is an ambiguity in an identification of the substance.

2. The detection apparatus according to claim 1, further comprising an arrangement for measuring the mobility of the ions.

3. The detection apparatus according to claim 1, wherein the ion modification is performed using a symmetrical ion modification field.

4. The detection apparatus according to claim 1, wherein the electrical arrangement is configured to perform the ion modification using a high voltage RF unit configured to apply an ion modification field.

5. The detection apparatus according to claim 4, wherein the ion modification field produced by the high voltage RF unit has a frequency of at least about 2 MHz.

6. The detection apparatus according to claim 4, wherein the ion modification field produced by the high voltage RF unit has a field strength of at least 10,000 V/cm.

7. The detection apparatus according to claim 1, wherein the ion modification is performed in short bursts.

8. The detection apparatus according to claim 7, wherein a length of the short bursts is about 1 μs.

9. The detection apparatus according to claim 1, further comprising a drift chamber.

10. The detection apparatus according to claim 9, wherein the electrical arrangement is configured to perform the ion modification on ions in the drift chamber.

11. The detection apparatus according to claim 1, further comprising a device configured to supply a dopant to the sample.

12. The detection apparatus according to claim 11, wherein the dopant is water.

13. The detection apparatus according to claim 1, wherein the electrical arrangement is configured to perform the ion modification so as to cause ion modification of only selected ones of the ions.

14. The detection apparatus according to claim 1, wherein the ion modification is fragmentation.

15. The detection apparatus according to claim 1, further comprising:
- an ionization region;
- a drift chamber;
- an inlet port configured to supply the sample to an ionization region;
- a gate separating the ionization region from the drift chamber;
- a row of electrodes disposed in the drift chamber; and
- a collector plate disposed in the drift chamber,
- wherein the ionizer includes a corona discharge device located in the ionization region, and
- wherein the electrical arrangement includes a high voltage RF unit configured to perform the ion modification on ions in the drift chamber.

16. The detection apparatus according to claim 15, further comprising a drift gas supply system configured to supply drift gas to the drift chamber such that the drift gas flows in a direction opposite a direction of a flow of the ions.

17. The detection apparatus according to claim 16, wherein the drift gas supply system includes a molecular sieve and a pump.

18. The detection apparatus according to claim 1, wherein the electrical arrangement includes at least one device configured to perform the ion modification selected from the group consisting of: a laser radiation device, a UV radiation device, a VUV radiation device, an infra-red radiation device, a photo ionization device, an electron bombardment device, an electron beam device, an electro spray device, an electron ionization device, a corona discharge device, a glow discharge device, a plasma emission device, and a radioactive emission device.

19. The detection apparatus according to claim 1, wherein the ions are individual molecular ions or ion clusters.

20. A method of using a detection apparatus to detect a substance in a sample, the method comprising:
- ionizing molecules of the substance using an ionizer; and
- performing ion modification on ions produced by the ionizer so as to cause ion modification of at least some of the ions;
- wherein the ion modification is performed only if the detection apparatus determines that there is an ambiguity in an identification of the substance.

\* \* \* \* \*